(12) United States Patent
Yamaki

(10) Patent No.: US 8,725,525 B2
(45) Date of Patent: May 13, 2014

(54) ENDOSCOPE SYSTEM

(75) Inventor: Masahide Yamaki, Hachioji (JP)

(73) Assignee: Olympus Corporation, Tokyo (JP)

(*) Notice: Subject to any disclaimer, the term of this patent is extended or adjusted under 35 U.S.C. 154(b) by 1493 days.

(21) Appl. No.: 11/104,886

(22) Filed: Apr. 13, 2005

(65) Prior Publication Data

US 2005/0228294 A1   Oct. 13, 2005

(30) Foreign Application Priority Data

Apr. 13, 2004   (JP) .................. 2004-118257

(51) Int. Cl.
*A61B 5/02*   (2006.01)
*A61B 5/04*   (2006.01)
*A61B 19/02*   (2006.01)
*H04N 5/14*   (2006.01)

(52) U.S. Cl.
USPC ............... 705/2; 348/701; 600/300; 600/478; 705/3

(58) Field of Classification Search
USPC ............. 386/95; 600/109; 348/68, 72, 701, 4, 348/620; 705/2, 3
See application file for complete search history.

(56) References Cited

U.S. PATENT DOCUMENTS

| | | | |
|---|---|---|---|
| 4,366,529 A * | 12/1982 | Takahashi et al. ................. | 362/4 |
| 4,938,205 A * | 7/1990 | Nudelman ..................... | 600/108 |
| 5,400,792 A | 3/1995 | Hoebel et al. | |
| 5,877,819 A * | 3/1999 | Branson ......................... | 348/701 |
| 6,002,425 A * | 12/1999 | Yamanaka et al. ............... | 348/68 |
| 6,215,517 B1 * | 4/2001 | Takahashi et al. ............... | 348/72 |
| 6,638,212 B1 * | 10/2003 | Oshima ......................... | 600/109 |
| 6,778,208 B2 * | 8/2004 | Takeshige et al. .............. | 348/65 |
| 6,791,601 B1 * | 9/2004 | Chang et al. .................... | 348/65 |
| 6,876,380 B2 * | 4/2005 | Abe et al. ....................... | 348/72 |
| 7,057,639 B2 * | 6/2006 | Spoonhower et al. .......... | 348/66 |
| 7,231,135 B2 * | 6/2007 | Esenyan et al. ................ | 386/95 |
| 7,395,249 B2 * | 7/2008 | Wang et al. ..................... | 706/14 |

FOREIGN PATENT DOCUMENTS

| | | |
|---|---|---|
| JP | 2002-34907 A | 2/2002 |
| JP | 2003-70748 | 3/2003 |
| JP | 2003-76786 | 3/2003 |
| WO | WO 01/88825 | 11/2001 |

OTHER PUBLICATIONS boazthesis_1.pdf—Boaz Patt, A Theory of Clock Synchronization, Massachusetts Institute of Technology, Oct. 17, 1994, MIT, 1994.*

* cited by examiner

*Primary Examiner* — Hiep V Nguyen
*Assistant Examiner* — Teresa Woods
(74) *Attorney, Agent, or Firm* — Scully, Scott, Murphy & Presser, P.C.

(57) ABSTRACT

The present invention relates to an endoscope system including: a real time clock; an interface for receiving medical information output from a peripheral device; and a control unit that adjusts clock information added to the received medical information into clock information of the real time clock when the peripheral device adds the clock information to the medical information, and adds clock information of the real time clock at a time of receiving to the received medical information when the peripheral device does not add the clock information to the medical information. According to the invention, even the medical information obtained from the different devices can be reproduced with data from the respective devices synchronized by associating the clock information based on the identical real time clock therewith. Consequently, even after the surgical operation, the contents of treatment performed during the surgical operation can be accurately reproduced.

12 Claims, 12 Drawing Sheets

ENDOSCOPE SYSTEM

CROSS-REFERENCE TO RELATED APPLICATION

This application is based upon and claims the benefit of priority from prior Japanese Patent Application No. 2004-118257, filed on Apr. 13, 2004, the entire contents of which is incorporated herein by reference.

BACKGROUND OF THE INVENTION

1. Field of the Invention

The present invention relates to an endoscope system for controlling medical equipment.

2. Description of the Related Art

In a surgical operation using an endoscope in the related art, an operator records an image of a state during a surgical operation in a recording device (hereinafter referred to as VTR), and confirms what kind of treatment he/she has performed from the movement of a treatment tool or from the state of a tissue after the surgical operation.

In the endoscope system, a preset number and times of outputs of an electric scalpel, the amount of air supply of an aeroperitoneum device, the change of the abdominal pressure of a patient can be stored as medical information, so that whether or not the surgical operation has been performed adequately can be confirmed.

Both of the above-described recording methods are effective as evidence of performance of the surgical operation. However, only one of the VTR and the medical information is not sufficient for understanding how the surgical operation has been performed at the time of confirmation after the surgical operation. If both can be associated with each other, the history of the surgical operation can be more accurately reproduced.

For example, in JP-A-2003-76786 and JP-A-2003-70748, a technology of taking an endoscopic image by a personal computer (PC) as digital data, distributing the endoscopic image via a network transmission together with medical information, and displaying them on the destination PC simultaneously is proposed.

In such a related art, since an endoscopic camera device, an aeroperitoneum device, a blood-pressure measuring device, an electric scalpel device which are peripheral devices are separately provided devices, timelag occurs often in clock information among the respective devices. There also exists delay time due to the communication. Therefore, there arises such a problem that when an image during the surgical operation is reproduced together with the medical information output from the respective peripheral devices after the surgical operation for confirmation, since the image information taken by the endoscope camera and the medical information showing the operating state of other peripheral devices cannot be synchronized with each other, an accurate information display cannot be obtained.

BRIEF SUMMARY OF THE INVENTION

Accordingly, an endoscope system is provided. The endoscope system includes a real time clock, an interface for receiving medical information output from a peripheral device, and a control unit that adjusts the clock information added to the received medical information into the clock information of the real time clock when the peripheral device adds the clock information to the medical information, and adds clock information of the real time clock to the received medical information when the peripheral device does not add the clock information to the medical information.

Such an effect that the clock information based on the identical real time clock is associated with all the received medical information even when the endoscope system receives medical information added with the clock information based on the different reference standards or when the endoscope system receives medical information which is not added with the clock information by the peripheral device.

Further, the endoscope system of the invention can include a plurality of the peripheral devices, and can further include a reproducing unit for reproducing the medical information received from the plurality of the peripheral devices synchronously based on the clock information adjusted or added by the control unit.

Since the medical information can be reproduced based on the clock information based on the identical real time clock, the plurality of medical informations can be reproduced synchronously. Therefore, there is such an effect that the contents of the treatment performed during the surgical operation can be accurately reproduced.

The endoscope system can further include a storage unit for storing the image information and the medical information separately, and a selecting unit for selecting whether the medical information is displayed so as to overlap with the image information, or so as not to overlap therewith when reproducing the image information in the reproducing unit.

Such an effect that an optimal screen display can be selected as needed since it is possible to reproduce the image information without displaying the medical information when the user wants to confirm only the image information, and display the medical information so as to overlap with the image information when the user wants to confirm the image information and the medical information simultaneously.

BRIEF DESCRIPTION OF THE SEVERAL VIEWS OF THE DRAWINGS

These and other features, aspects, and advantages of the apparatus and methods of the present invention will become better understood with regards to the following description, appended claims, and accompanying drawings where:

DETAILED DESCRIPTION OF THE INVENTION

Embodiments will be described below with reference to the accompanying drawings.

Referring now to FIG. 1 to FIG. 7, an endoscope system according to a first embodiment will be described.

Figure 1:
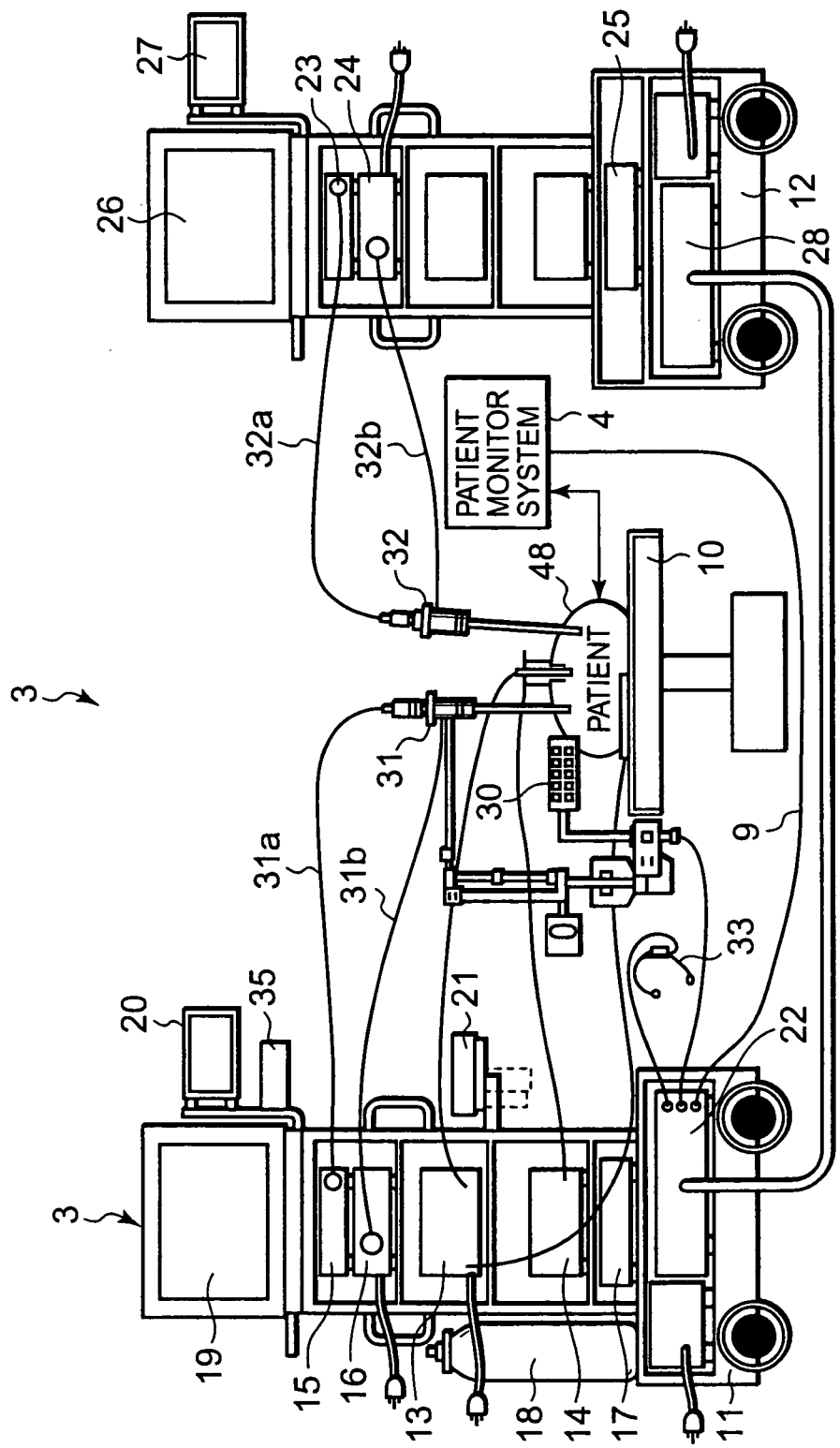
FIG. 1 is a drawing showing a structure of an endoscopic surgical operation system according to a first embodiment.

Referring to FIG. 1, the entire structure of an endoscopic surgical operation system 3 to be disposed in an operating room 2 will be described.

As shown in FIG. 1, the operating room 2 includes a patient bed 10 on which a patient 48 lies, and the endoscopic surgical operation system 3 disposed therein. The endoscopic surgical operation system 3 includes a first cart 11 and a second cart 12.

The first cart 11 includes medical equipment as controlled devices, such as an electric scalpel device 13, an aeroperitoneum device 14, an endoscopic camera device 15, a light source device 16, and a video tape recorder (VTR) 17, and a gas cylinder 18 filled with carbon dioxide disposed thereon. The endoscopic camera device 15 is connected to a first endoscope 31 via a camera cable 31a. The light source device 16 is connected to the first endoscope 31 via a light guide cable 31b.

The first cart 11 includes a display device 19, a first centralized display panel 20, and an operating panel 21 placed thereon. The display device 19 is, for example, a TV monitor for displaying the endoscopic image or the like.

The centralized display panel 20 is a display unit which can selectively display any data during the surgical operation. The operation panel 21 includes a display unit such as a liquid crystal display and, for example, a touch sensor provided integrally on the display unit, and configured as a centralized operating device which is operated by a nurse located in a non-sterilized area.

The first cart 11 includes a system controller 22 as a control device placed thereon. The electric scalpel device 13, the aeroperitoneum device 14, the endoscopic camera device 15, the light source device 16, and the VTR 17 are connected to the system controller 22 via a communication cable (not shown). The system controller 22 is adapted to connect a headset type microphone 33, and the system controller 22 recognizes voice input from the microphone 33 and controls the respective devices by the voice of the operator.

The first cart 11 is provided with a RFID (Radio Frequency Identification) terminal 35 which can write/read individual ID information of an object via radio transmission by an ID tag embedded in a treatment tool such as the first endoscope 31 or the electric scalpel device 13.

On the other hand, the second cart 12 includes an endoscopic camera device 23 which is a controlled device, a light source device 24, an image processing device 25, a display device 26, and a second centralized display panel 27 placed thereon.

The endoscopic camera device 23 is connected to a second endoscope 32 via a camera cable 32a. The light source device 24 is connected to a second endoscope 32 via a light guide cable 32b.

The display device 26 displays the endoscopic image or the like captured by the endoscopic camera device 23. The second centralized display panel 27 can selectively display any data during the surgical operation.

The endoscopic camera device 23, the light source device 24, and the image processing device 25 are connected to a relay unit 28 placed on the second cart 12 via a communication cable (not shown). The relay unit 28 is connected to the system controller 22 placed on the first cart 11 via a relay cable 29.

Therefore, the system controller 22 is adapted to perform centralized control on the camera device 23, the light source device 24 and the image processing device 25, which are mounted on the second cart 12, the electric scalpel device 13, the aeroperitoneum device 14, the camera device 15, the light source device 16, and the VTR 17, which are mounted on the first cart 11. Therefore, when the system controller 22 is communicated with these devices, the system controller 22 can display the setting state of the connected devices or the setting screen for operating switches or the like on the liquid crystal display of the aforementioned operating panel 21. In addition, the system controller 22 is adapted to be capable of input operation such as change of the setting value by touching the operating switch and operating the touch sensor of a predetermined area.

A remote controller 30 is a second centralized operating device that a surgeon who is in a sterilized area operates. It is adapted in such a manner that the surgeon can operate the other devices in communication via the system controller 22.

The system controller 22 is connected to a patient monitor system 4 via a cable 9, and as described later, is capable of analyzing information on the living body obtained from the patient monitor system 4, and displaying the result of analysis on the specific display device.

An infrared ray communication port (not shown) as a communication means is mounted to the system controller 22. The infrared ray communication port is provided at a position at which the infrared ray can easily be irradiated, such as a position in the vicinity of the display device 19, and is connected to the system controller 22 via a cable.

Figure 2:
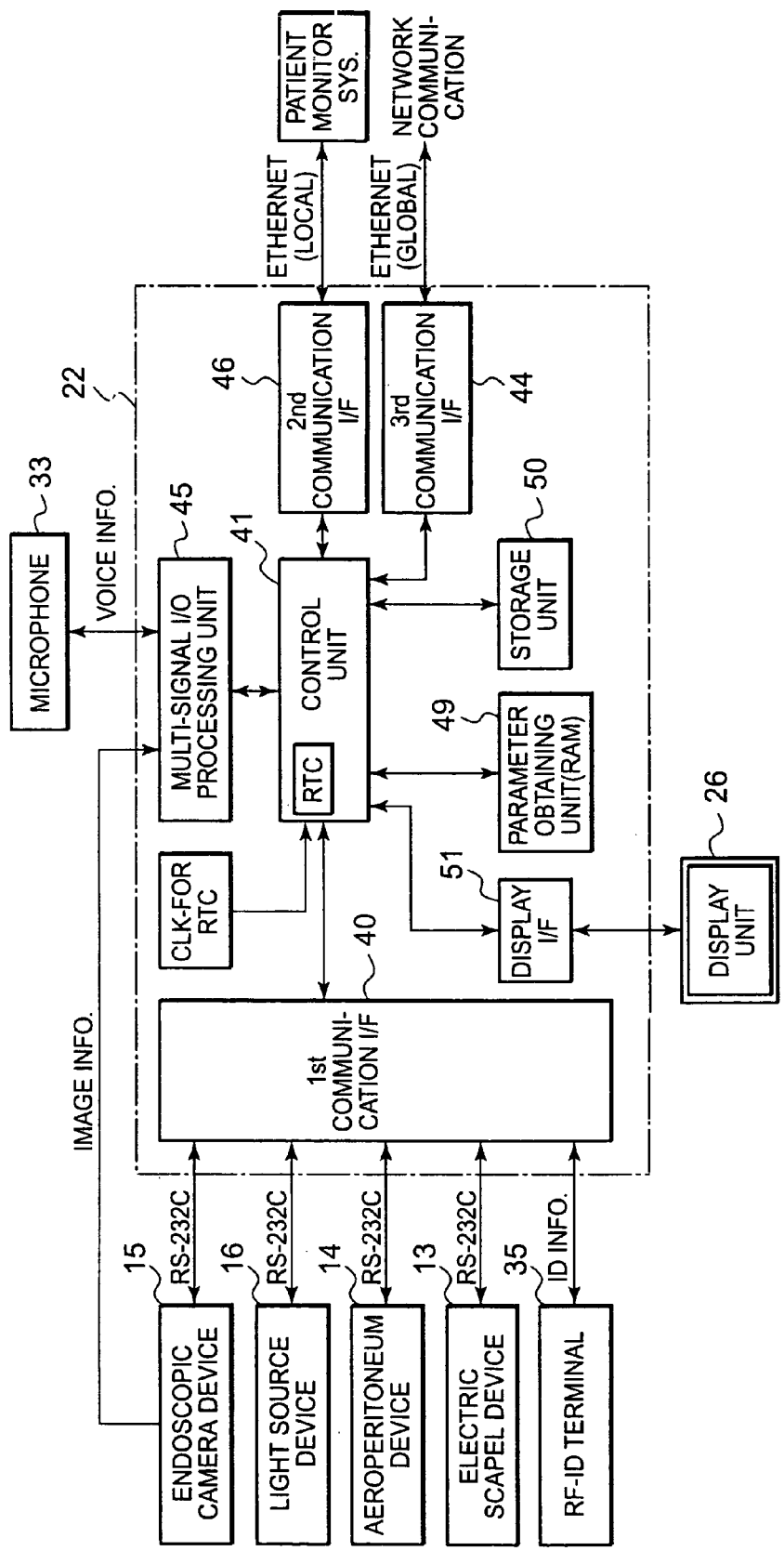
FIG. 2 is a block diagram showing a structure of the system controller of FIG. 1.

As shown in FIG. 2, the system controller 22 includes a real time clock (RTC), a control unit 41 for adjusting or adding clock information, and a first communication interface (I/F) 40 for performing a serial communication of RS-232C with respect to the peripheral devices such as the endoscopic camera device 15, the light source device 16, the aeroperitoneum device 14, and the electric scalpel device 13 for receiving medical information output from the peripheral devices.

The RFID (Radio Frequency Identification) terminal 35 can read and write the individual ID information of the object contained in the ID tag embedded in the first endoscope 31, a treatment tool of the electric scalpel device 13, or chemical agent via radio transmission. The user can leave a history of treatment done by the operator or the nurse by associating the read individual ID information with a vital sign, a device parameter history, and a time axis of the image.

In this embodiment, the RTC is provided also on the endoscopic camera device 15 or the like for performing communication via the respective communication I/F, and a common I/F is also provided.

Although the system controller 22 of the present embodiment is adapted to perform RS-232C serial communication via the first communication I/F 40, it is also possible to perform communication between the endoscopic camera device 15 and the light source device 16, the aeroperitoneum device 14, the electric scalpel 13 by network communication via Ethernet®, radio communication such as Bluetooth, or infrared ray communication.

The system controller 22 includes a multi-signal I/O processing unit 45 for performing pick-up processing of endoscopic images taken by the endoscopic camera device 15 (general capturing process or A/D, D/A conversion process), or recording (compressing or decompressing process) of conversation in the surgical operating room through the microphone 33 or the like, or making comment of the operator during the surgical operation into a text (speech recognition process).

The control unit 41 allows communication with the patient monitor system 4 via a second communication I/F 46. The second communication I/F 46 is an I/F for performing communication with a device to which a local IP address is allocated.

The communication by the second communication I/F 46 may be a LAN network communication of the TCP/IP protocol or UDP protocol, or a serial communication such as a USB or RS-232C.

The control unit 41 is connected to a third communication I/F 44 communicable with an Internet or a PC (not shown) at a remote location, such as in another hospital. Here, the third communication I/F 44 is an I/F for performing communication with a device to which a global IP address is allocated.

The control unit 41 is connected to a parameter obtaining unit 49 for obtaining medical information of the peripheral device obtained via the aforementioned respective communication I/Fs or image/voice information and to a storage unit 50 for storing medical information of the peripheral device for a predetermined period or the image/voice information. The parameter obtaining unit 49 is composed of a work memory such as a RAM.

The control unit 41 can display the medical information of the peripheral device or the image/voice information on the display unit 26 as the reproducing unit via a display I/F 51.

Figure 3:
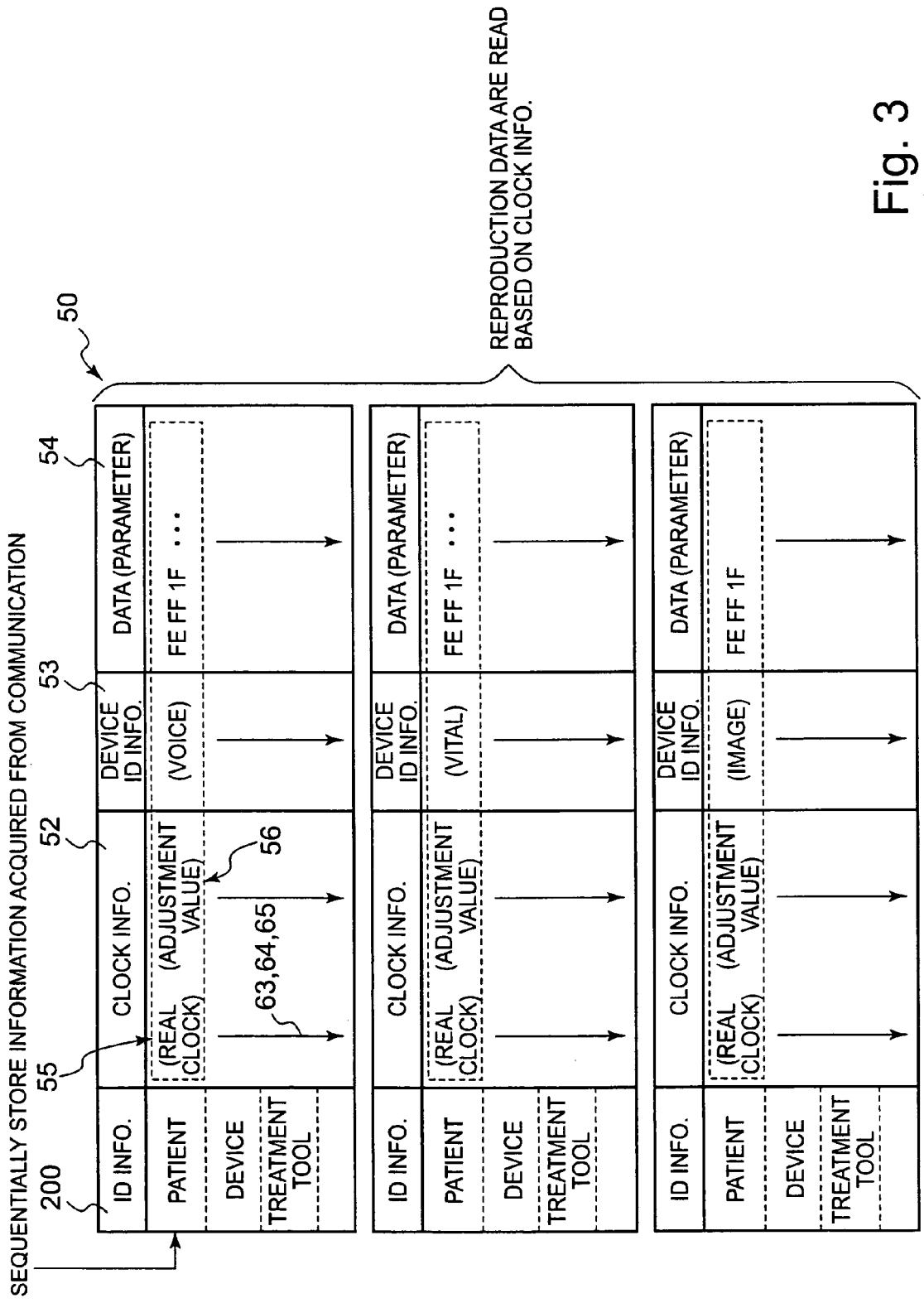
FIG. 3 is a drawing showing a structure of a storage area of the storage unit of FIG. 2.

As shown in FIG. 3, the storage unit 50 constitutes a storage area by a header information area 200 for storing identification information for identifying the obtained information (device information, patient information, individual ID information in terms of category), a clock information area 52 for storing the clock information, a device ID area 53 for storing the device ID information, for example, when controlled by ID, and a data area 54 for, for example, the preset value/measured value.

The identification information is used at a time of extracting desired data for obtaining information such as the patient data, or information on the device maintenance, or the treatment tool.

General address control is performed in the storage unit 50, which is an electrically readable/writable memory. The storage unit 50 is constructed, for example, of a flash ROM (smart media or Compact Flash®) or HDD.

The storage unit 50 can store the voice data, the image data, the device parameter, the patient information into the specified data areas 54 as shown in FIG. 3. When the user reproduces the image/voice, he/she can read out the data from the specified data area 54, and reproduce and display it on the display device 26 or the like.

In this embodiment, a portion for storing the data corresponds to the storage unit 50 in the system controller 22. However, it is also possible to configure the storage unit by a storage unit which can be attached and detached freely such as those of USB or ATA card-type, and transfer the storage unit to a separate PC or the like for reproduction.

The clock information area 52 is configured of an area for storing a real clock information 55 calculated by calculation described later and an adjustment value 56 (for example, a value obtained by adding the timelag of communication when the respective medical informations are obtained and the timelag of RTC between the respective peripheral devices and the system controller 22.

Figure 5:
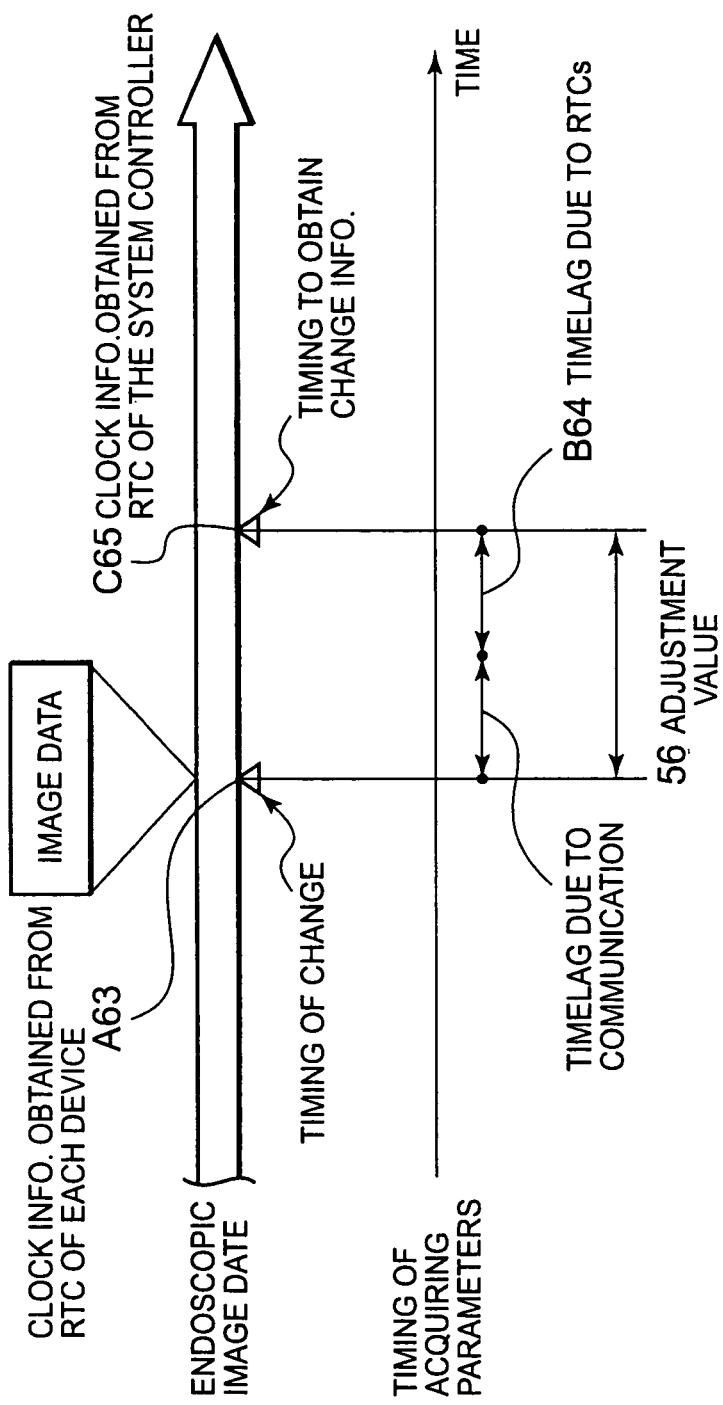
FIG. 5 is a drawing showing a timing of action initiation of the electric scalpel of FIG. 1.

Referring now to FIG. 5, reference numeral 63 is clock information A obtained from the RTC on the side of the respective devices. Reference numeral 64 designates a timelag B of the RTCs between the respective devices and the system controller 22 for calculating the adjustment value, which is obtained in advance when initializing the system. Reference numeral 65 designates clock information C obtained from the RTC on the side of the system controller 22 when the latest clock information of the respective device is obtained.

Figure 4:
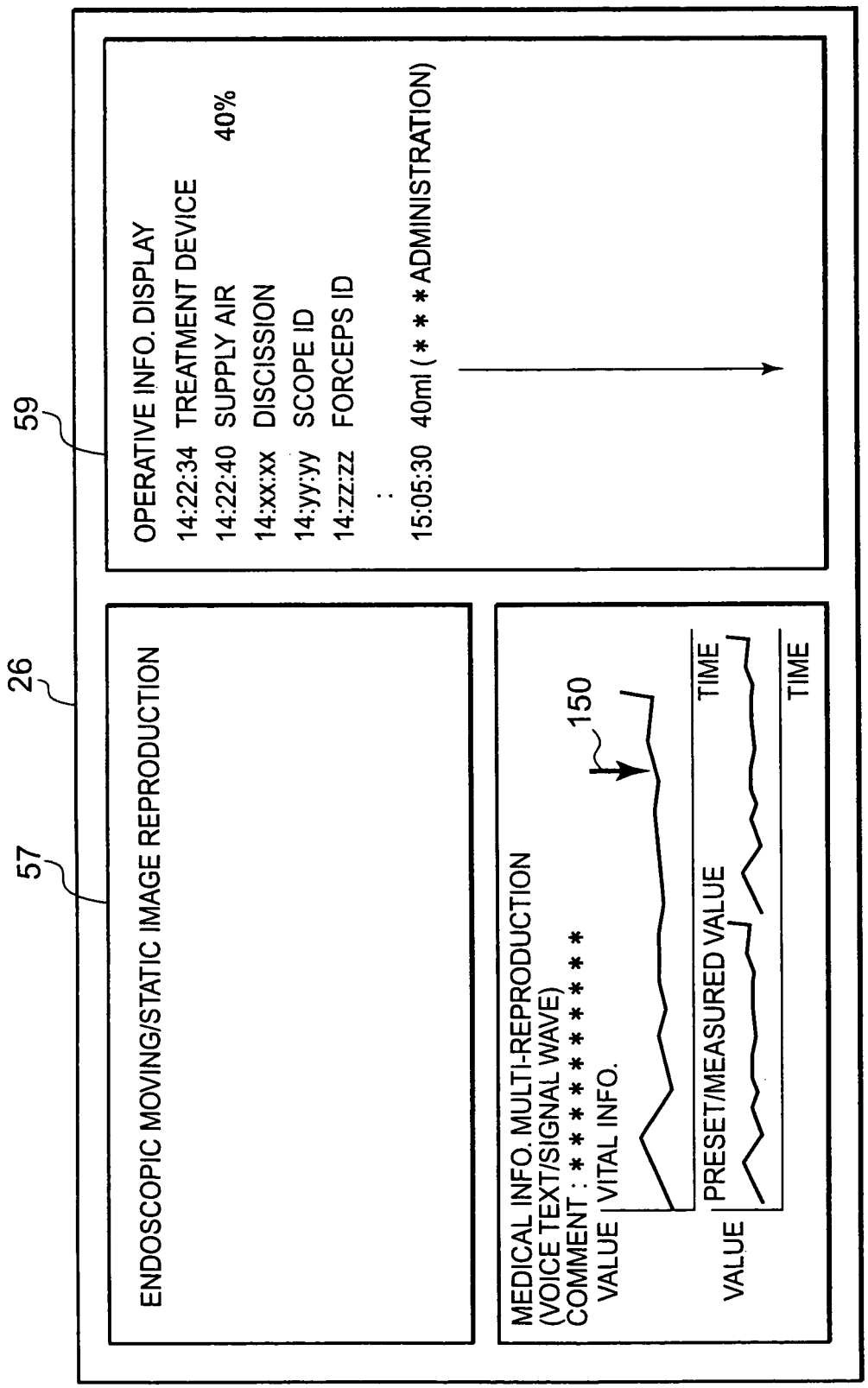
FIG. 4 is a drawing showing an example of a display layout in the display device of FIG. 1.

FIG. 4 is an example of a layout when reproducing medical information and image/voice data by a display device 26 described above. The display device 26 is a display such as CRT, LCD, or PDP. In FIG. 4, the layout structure includes an endoscopic image reproduction area 57 for displaying the endoscopic image in PinP (picture in picture) manner, a medical information multi-reproduction area 58 for multi-reproduction medical information such as information on living body, and a parameter value display area 59 for displaying medical information such as the parameter of the respective peripheral devices.

As shown in FIG. 4, the medical information multi-reproduction area 58 can display the change of the vital sign data with time obtained from the patient monitor system 4 and the change of the operation preset value/measured value of the respective medical devices with time by a waveform. The medical information multi-reproduction area 58 can display the obtained voice data in a text.

In the medical information multi-reproduction area 58, the user can store images or parameters which he/she wants to associate with into the storage unit 50 in conjunction with the time axis by specifying a cursor 150 to the time axis on the display using a pointing device (not shown) such as a mouse (not shown) or a touch panel. Also the user can reproduce/display the image or parameter associated by the user on the endoscopic image reproduction area 57 or the parameter value display area 59.

The parameter value display area 59 displays/revises the latest information (stored in the parameter obtaining unit 51) including the operational information obtained by the system controller 22 via the communication with the respective devices on a real time basis.

Referring back to FIG. 5, the same shows a time flow on a lateral axis for explaining the respective timings of action initiation. The image data in FIG. 5 is an endoscopic video display at timings when the operator caused the electric scalpel to output. The content of the image of the image data is an image of a scene where the output electric scalpel incises a tissue. This timing is designated by clock information A63 obtained from the RTCs of the respective devices.

Subsequently, the time that the system controller 22 obtains the medical information which indicates that the incision output is performed via the communication is designated as a timing for obtaining the change of output from the electric scalpel, and the clock information obtained from the RTC of the system controller 22 at this time is represented by C65. The delay time (timelag) due to communication and the timelag of clock information between the RTCs of the respective devices and the RTC of the system controller 22 are contained between the clock information A63 and the clock information C65.

In other words, by adjusting these two timelags, the real clock information synchronized with the image data can be obtained. The value obtained by summing these two timelags is the adjustment value 56.

Subsequently, the actual operating sequence will be described.

First, preparation of the endoscopic surgical operation is performed. The nurse transports a patient 48 on a bed 10 in advance, and an anesthesiologist administers anesthetic. The operator confirms a clinical record of the patient and the technique. The nurse helps the patient 48, assists administration of anesthetic, performs installation of devices, preparation of equipment to be used (not shown), connection of the endoscope, the air-supply tube, and so on, whereby the endoscope system shown in FIG. 1 is prepared as shown therein. The system controller 22 and the respective devices, and the patient monitor system 4 are also activated.

Figure 6:
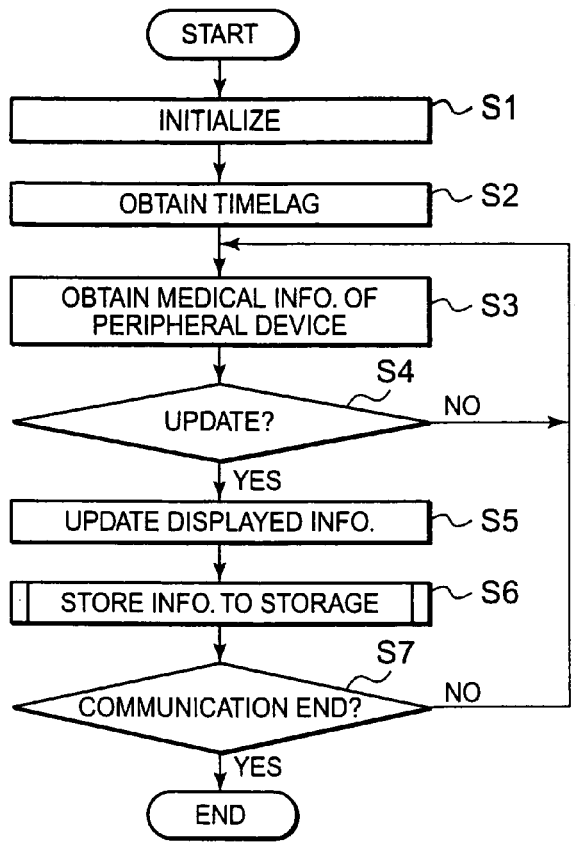
FIG. 6 is a flowchart showing an operation of the system controller of FIG. 2.

Then, as shown in FIG. 6, in Step S1, the system is initialized. First, the system controller 22 establishes communication with respect to the devices which it can communicate with. Then, the system controller 22 obtains the clock information of the respective devices, and calculates the difference from the clock information in the system controller 22.

In Step S2, the system controller 22 obtains the difference between the clock information of the respective devices and the system controller 22 (the timelag of the RTC for calculating the adjustment value will be represented by B64, hereinafter), and stores the same in the storage unit 50.

In step S3, the medical information of the peripheral devices is obtained.

In step S4, when there is any update of the medical information, the system controller 22 revises the medical information displayed on the display device 26 in Step S5, and then the medical information is stored in the storage unit 50 in sequence in Step S6.

When the communication is terminated in Step S7, the communicating operation is ended in Step S8, and if not, the communication with the respective devices is continued in sequence.

Figure 7:
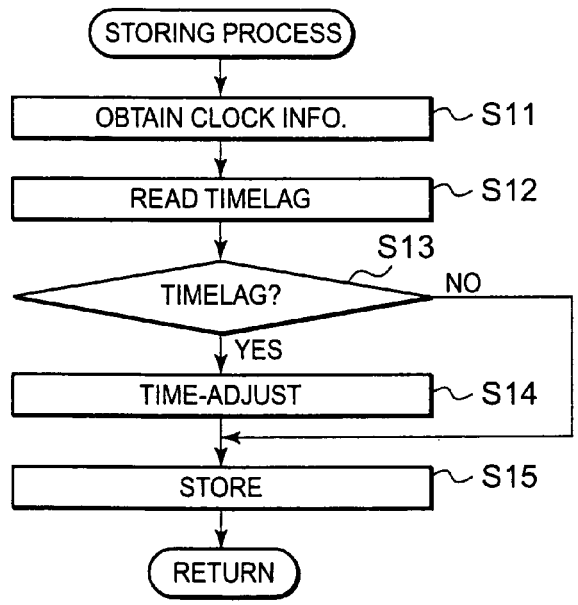
FIG. 7 is a flowchart showing a storing process for performing a sequential storage of FIG. 6.

Referring now to FIG. 7, the operation of the storing process for sequential storage (the subroutine of the storing process in Step S6 in FIG. 6) will be described.

As shown in FIG. 7, in Step S11, the system controller 22 obtains the clock information A63 (see the parameter structure/packet structure in FIG. 9, described later) from the RTC of the respective devices. Subsequently, in Step S12, the system controller 22 reads the timelag B64 of RTC for calculating the adjustment value which is obtained in initialization of the system (Step S1 in FIG. 6) from the storage unit 50. Then, the system controller 22 obtains the clock information C65 obtained from the RTC of the system controller 22 when the latest clock information of the respective devices are obtained.

The A63, B64, and C65 are associated with the respective devices.

In Step S13, the system controller 22 determines whether or not timelag occurs in clock information. The term "timelag" used here does not include the case in which time required for communication does not exceed a certain time t. In other words, when it does not exceed the time t, it is considered that revision is done on a real time basis. When the communication time exceeds the time t, it is considered that there is "timelag".

For example, the following expression is established.

timelag (occurred)=time required for communication (clock information $C$−clock information $A$−timelag $B$)>$t$ When the system controller 22 recognizes that the timelag occurs, the system controller 22 calculates a new adjustment value added with the above-described timelag in Step S14. Then, the real clock information of the cock information obtained at the respective timings is calculated based on the new adjustment value.

For example, the adjustment value 56 at the time where the respective medical information is obtained=(timelag B of RTC+timelag due to communication)

The real clock information A55=clock information C+adjustment value 56 (it may be: clock information C−clock information A).

In Step S15, the real clock information and the adjustment value, and the obtained medical information are stored for each parameter in Step S15.

Subsequently, in the reproduction process, as shown in FIG. 3, reproduction is performed synchronously based on the real clock information of the stored image data, the real clock information of the voice data, and the real clock information of the medical information.

In this embodiment, the voice data and the image data are input to the system controller 22 directly, and not via communication. Therefore, since data transfer is performed in a very short time in comparison with the data transfer via communication, the delay time which is required for communication is not adjusted. However, when data is obtained via communication or when it takes time for processing, the adjustment process can be performed in the same manner as in the case of the medical information for the respective devices.

In this manner, according to this embodiment, medical information output from the different peripheral devices, such as the endoscopic image, information on the surgical operation devices, or patient information, is collected to the system controller 22.

The system controller 22 can adjust the aforementioned clock information to the clock information based on the identical real time clock, store and display the result even when the clock information based on the different standard is added to the medical information received from the different peripheral devices. Therefore, since the image information and the medical information can be reproduced synchronously, reliability as a history of information on medical processing can be advantageously improved.

Figure 8:
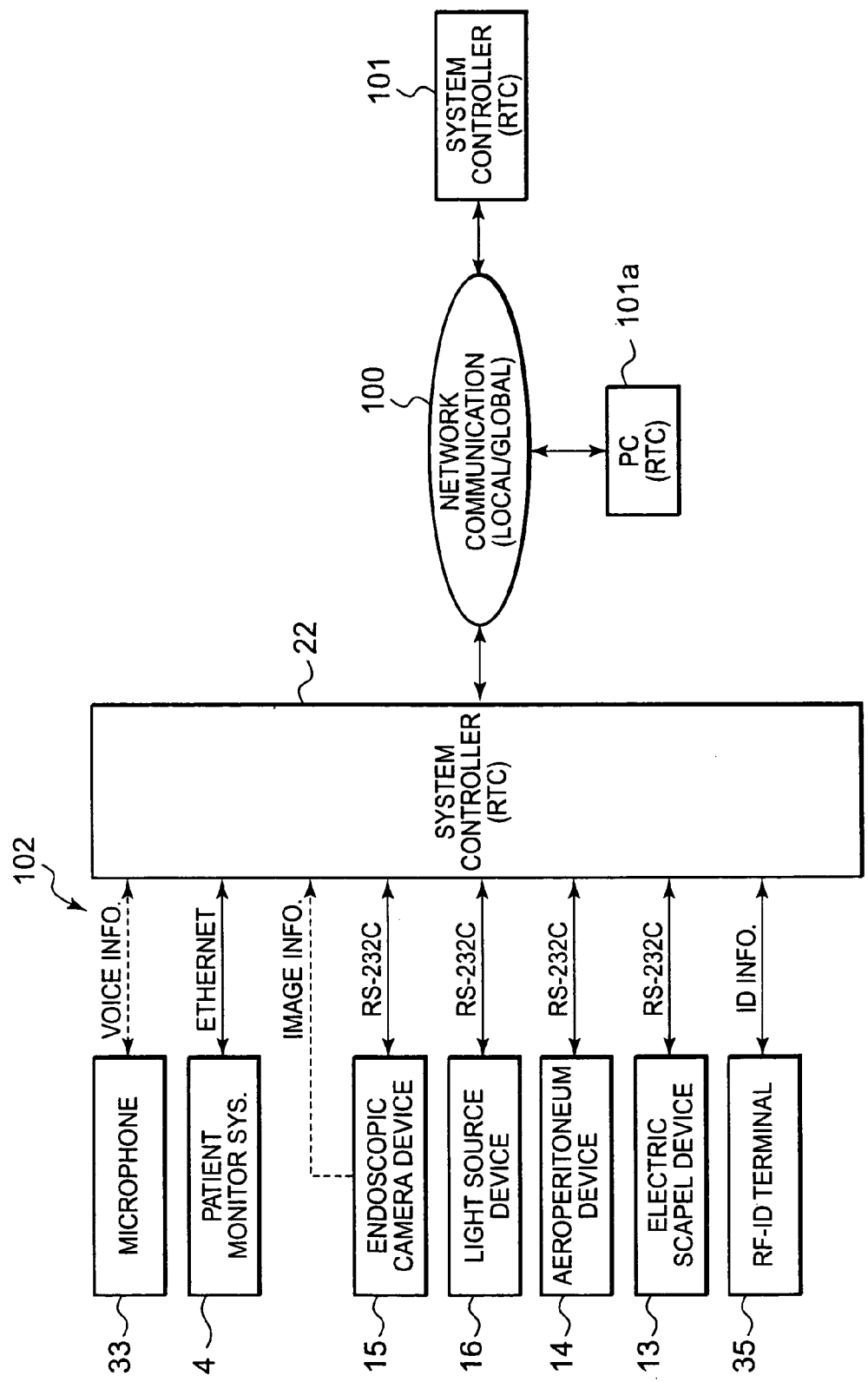
FIG. 8 is a drawing showing a structure of an endoscopic surgical operation system according to a second embodiment.
Figure 9:
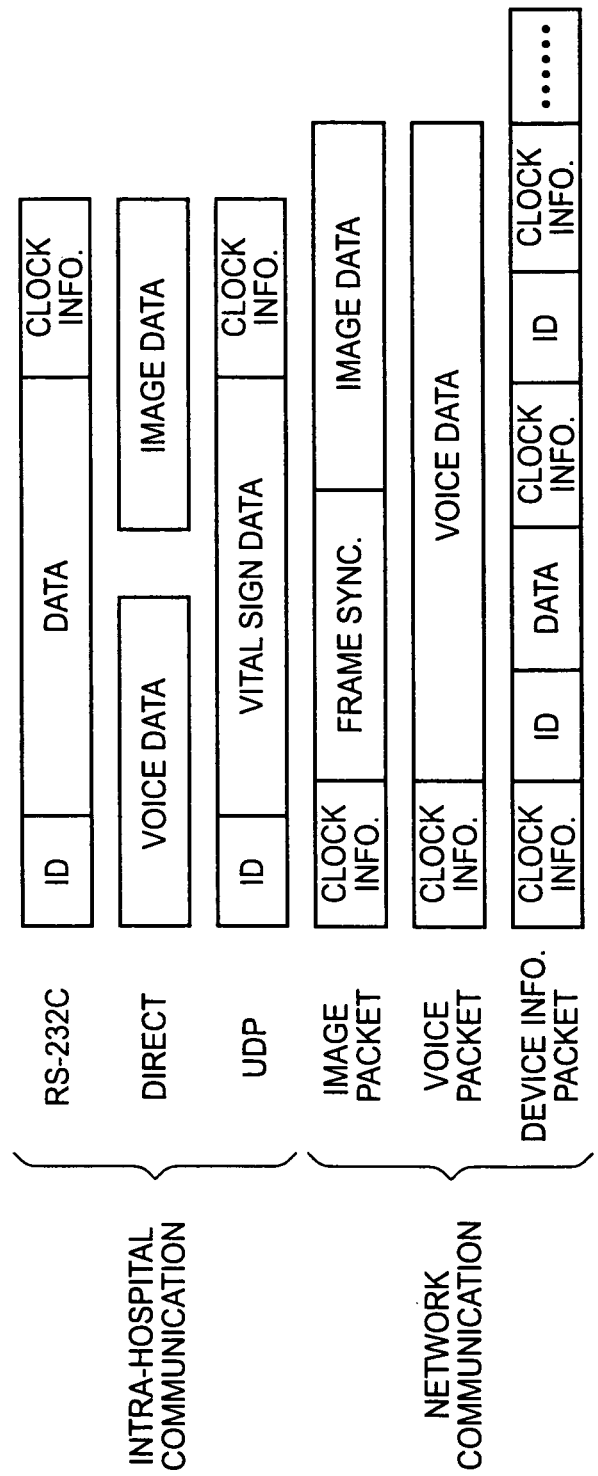
FIG. 9 is a drawing showing a data structure of communication data in the endoscopic surgical operation system of FIG. 8.
Figure 10:
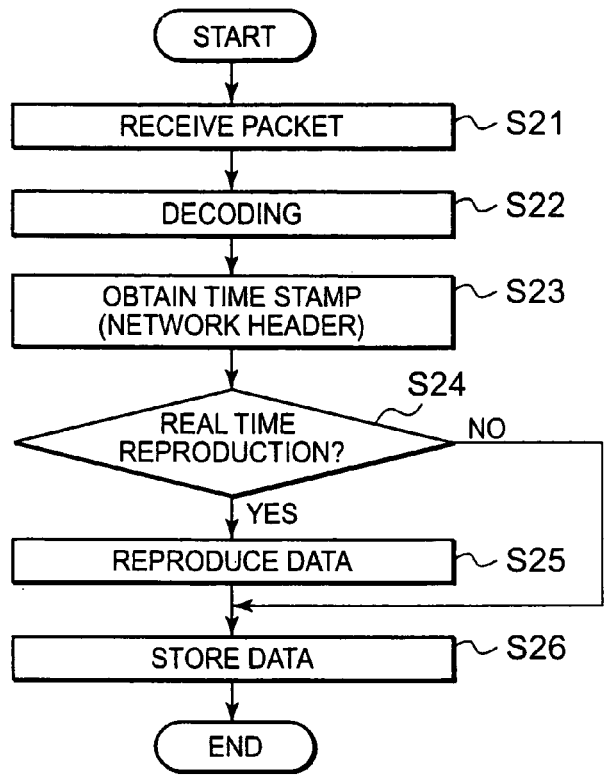
FIG. 10 is a flowchart for explaining the operation of the second system controller of FIG. 8.

Referring now to FIG. 8 to FIG. 10, an endoscope system according to a second embodiment will be described.

FIG. 8 is a drawing showing a structure of the endoscopic surgical operation system. FIG. 9 is a drawing showing a data structure of communication data in the endoscopic surgical operation system in FIG. 8. FIG. 10 is a flowchart explaining the operation of the second system controller in FIG. 8.

In the second embodiment, only the points which are different from the first embodiment will be described, and the same structures are represented by the same reference numerals, and description thereof is omitted.

FIG. 8 shows a system in which the system controller 22 described in FIG. 2 in the first embodiment can communicate with a second system controller 101 or a multipurpose PC 101a inside/outside the hospital through a network communication 100, and then transfer the medical information to a remote location or obtain the operation/support information from the remote location.

In this embodiment, a case in which there is no clock information in the part of the information which can be obtained from the respective I/Fs is assumed. In other words, it is assumed that part of the devices have no RTC. Therefore, this system is adapted to add the clock information received from the RTC in the system controller 22 to the medical information obtained from the respective devices. It is needless to say that the added clock information can be stored in the storage unit 50 and reproduced again.

Furthermore, according to the present embodiment, as shown in FIG. 8, the aforementioned system controller 22 and the respective devices 13-16 transmit the medical information via the serial communication of RS-232C, and the system controller 22 and the patient monitor system 4 transmits the medical information by the network communication via the Ethernet®.

As in the first embodiment, the system controller 22 is adapted to receive the voice information from the microphone 33 in analogue/digital form, receive the image information from the endoscopic camera device 15 in analogue/digital form via the image communication, and receive the individual ID information from RFID terminal 35 via the radio communication.

Hereinafter, the serial communication of the aforementioned RS-232C, the network communication via the Ethernet®, the voice communication, the image communication, and the radio communication are referred to as in-house communication 102.

FIG. 8 shows an endoscopic surgical operation system configured of the system controller 22 and an outdoor second system controller 101 and the multipurpose PC 101a, they can establish the network communication 100 via the protocol such as TCP/IP or UDP.

The in-house communication 102 represents transmission of the directly input image/voice data described in the first embodiment, or the parameter of the respective devices obtained by communication, or vital sign data (see in-house communication in FIG. 9 as regards the structure of the communication data).

The network communication 100 transmits the directly input image/voice data described in the first embodiment and information of the respective devices obtained by communication to one or more devices (the second system controller 101 or the multipurpose PC 101a) by the network protocol (which is the aforementioned TCP/IP or UDP, see network communication in FIG. 9).

FIG. 9 shows a basic concept of the data structure when transmitting and receiving the medical information between the system controller 22 and the respective devices in the in-house communication 102 and the network communication 100. In particular, by employing the network communication 100 in a packet mode, the image, voice, ID, and device information can be distributed based on the clock information of the same RTC adjusted or added by the control unit of the system controller 22.

FIG. 10 is a flowchart of the operation of the control unit (not shown) in the second system controller 101 shown in FIG. 8.

The system controller 22 obtains the medical information in a state of the in-house communication 102 in FIG. 9. In FIG. 9, information obtained from the devices having the RTC provided therein is shown. However, when the system controller 22 obtains information from some devices having no RTC, the clock information from the RTC of the system controller 22 is added to the data at the time when the system controller 22 obtained the information.

The system controller 22 communicates with the second system controller 101 via the protocol, such as the RTP. In such a case, the system controller 22 adds the clock information at a timing of transmission from the system controller 22 to the second system controller 101 (hereinafter, referred to as a time stamp, which is different from the clock information obtained from the respective devices or the clock information added by the system controller 22) as header information of the packet to the data and sends the packet data.

In the second system controller 101, the packet reception is performed in Step S21 in FIG. 10, the received packet is decoded in Step S22, and the time stamp is obtained in Step S23.

Here, when the device on the receiving side is the second system controller 101, the data can be reproduced on a display device (not shown) connected to the second system controller 101. When the device on the receiving side is the PC 101a, the data can be reproduced on a liquid crystal monitor associated with the PC.

Subsequently, in step S24, the user determines whether or not the real time reproduction is to be performed. When the user determines to perform the real time reproduction, the device on the receiving side reproduces the data in sequence based on the time stamp information in step S25.

In this manner, the time stamp is necessary because the order that the device on the receiving side receives the packet data including the image/voice/device parameter via the network communication 100 is different from the order that the system controller 22 transmits the packet data.

If the user stores the data instead of performing the real time reproduction in Step S24, the control unit calculates and stores the real clock information as described in the first embodiment based on the time stamp added to the header, the clock information of the respective devices obtained in the respective devices having the RTC, the adjustment value, and the clock information of the system controller 22 in Step S25.

In this arrangement, the device on the receiving side can adjust the timelag in the in-house communication 102 and the timelag of the network communication occurred due to the network communication 100 in FIG. 8.

When there are a plurality of devices on the receiving side, which are connected to the network communication 100, the extent of the lag of the clock information in the network communication 100 in FIG. 8 increases. However, by causing the adjustment process to be performed for each device on the receiving side, storage/reproduction process without lag is achieved.

In this manner, according to this embodiment, since the data can be distributed with the clock information which enables adjustment process on the receiver side even when the medical information is distributed via the network communication, a history of the medical information with high reliability can be recorded for each receiving device in addition to the effect of the first embodiment.

Figure 11:
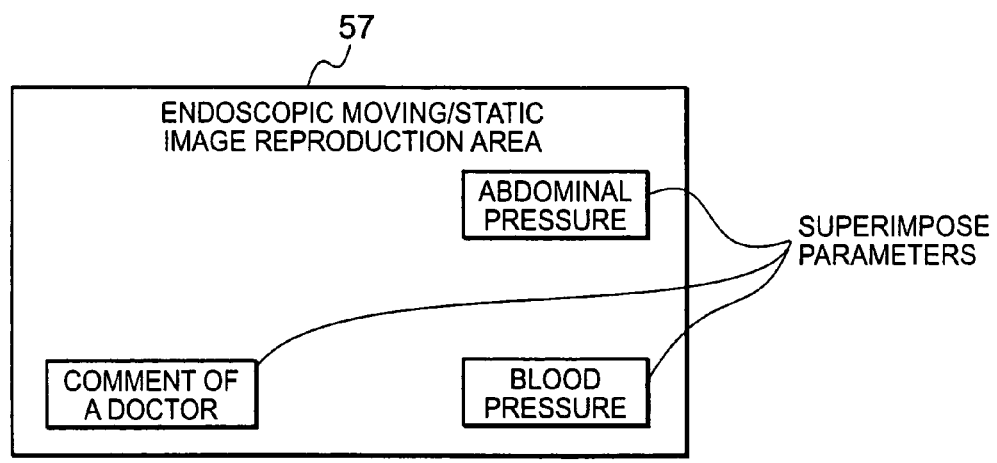
FIG. 11 is a drawing showing an example of a display layout when reproduced on a display device or a liquid crystal monitor on a PC according to a third embodiment.

Referring now to FIG. 11, the endoscope system according to the third embodiment will be described.

FIG. 11 is a drawing showing an example of the display layout of reproduction on the display device 26 or the liquid crystal monitor (not shown) associated with the PC 101a.

The third embodiment will be described only where the same differs from the first or second embodiments. The same structures are represented by the same reference numerals, and description thereof will be omitted.

FIG. 11 shows a second layout example of reproduction on the display device 26 or the liquid crystal monitor on the PC 101a described in the first embodiment or the second embodiment. The third embodiment is an embodiment in which the medical information is displayed by a superimposing process in order to obtain a larger reproduction area for the endoscopic image.

In this case, the abdominal pressure obtained from the aeroperitoneum device 14, the blood pressure obtainable from the patient monitor system 4, and text data obtained from the voice data input which is a comment of the doctor, are displayed in a superimposed manner.

When the term "superimpose" is used in terms of analogue mode, the medical information such as the parameter information is displayed after being overwritten on the image data. Therefore, when the medical information is not necessary, it may not be displayed in a non-display mode. However, according to the third embodiment, since the image data/voice data/parameter data of the respective devices are stored separately as shown in the first embodiment, the ON/OFF operation of the superimpose or selection of the superimposed data (preset value/measured value/error information) can be performed on the operating panel 21, which is a selection unit.

In this embodiment, since the surgical operator wants to concentrate on the endoscopic image during the surgical operation, the superimposing process is remained OFF and is turned ON when an error of the respective device occurs.

At this time, the image data/voice data/parameter of the respective devices are stored in the storage unit 50 shown in FIG. 1 together with the real clock information.

Therefore, when the user reproduces the stored information after having completed the surgical operation, the user can reproduce only the endoscopic image, reproduce in a superimposed manner, or bring the superimposing of the error information into an OFF state.

In this manner, according to this embodiment, in addition to the effects in the first and second embodiment, since unintentional reduction of the size of the important endoscopic image or missing of part of the image due to superimposition of the parameters during surgical operation can be avoided, the doctor can advantageously observe the image in a desired state. Also, after the surgical operation, reproduction can be performed while associating the parameters of the respective devices to avoid the timelag.

Figure 12:
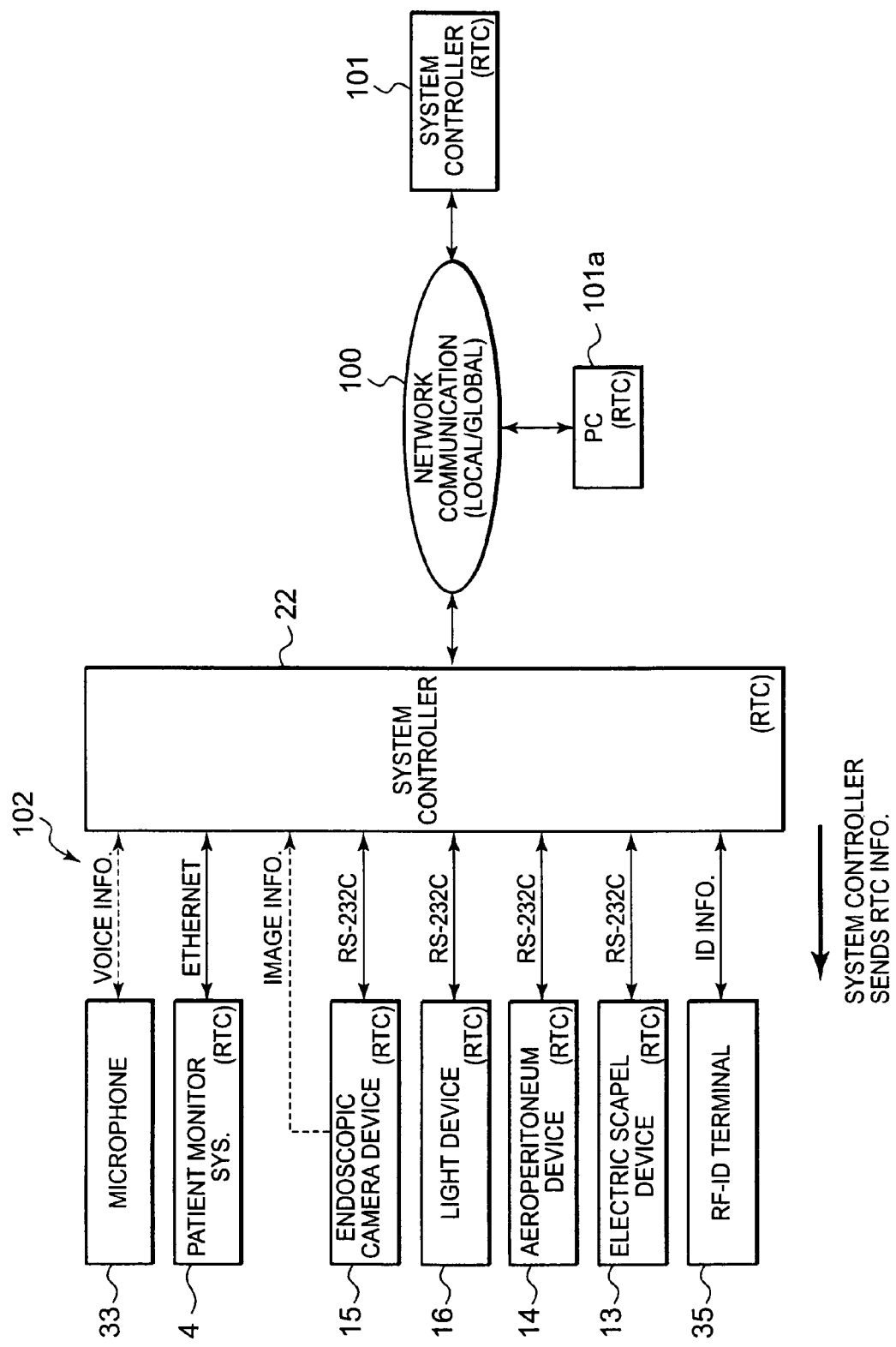
FIG. 12 is a drawing showing a structure of an endoscopic surgical operation system according to a fourth embodiment.

Referring now to FIG. 12, the endoscope system according to a fourth embodiment will be described.

The fourth embodiment will be described only where the same differs from the second embodiment, and the same structures are represented by the same reference numerals and description will be omitted.

This embodiment is an embodiment in which the respective devices have the clock information and the clock information can be transmitted to the respective devices based on the RTC in the system controller 22. FIG. 12 shows a system structure in which the clock information of the system controller 22 is transmitted to the respective peripheral devices 4, 13-16, and the respective devices adapt their own RTC information to the RTC of the system controller 22 based on the RTC information of the system controller 22, and data transmission is performed based on the identical RTC.

In the present embodiment, when the endoscopic surgical operation system 3 is activated to establish the communication with the respective peripheral devices, the clock information from the system controller 22 is transmitted to the respective peripheral devices. The respective peripheral devices adjust the clock information of their own based on this clock information. Accordingly, the clock informations of the respective peripheral devices coincide with the clock information of the system controller 22. When the change of the parameter occurs in the respective peripheral devices, the change of the parameter can be transmitted together with the clock informations of the respective devices which coincide with the clock information of the system controller 22. Since the system controller 22 or the PC 110*a* can recognize or store the clock information of the parameters obtained via the communication as in the first embodiment, reproduction is ensured irrespective of the lag of the RTC among the respective peripheral devices or the lag due to the communication.

In this manner, in the present embodiment, in addition to the effects of the second embodiment, the lag between the medical informations of the respective peripheral devices and the data of the endoscopic image can be easily eliminated by the distribution to destinations based on the clock information of the system controller 22.

Figure 13:
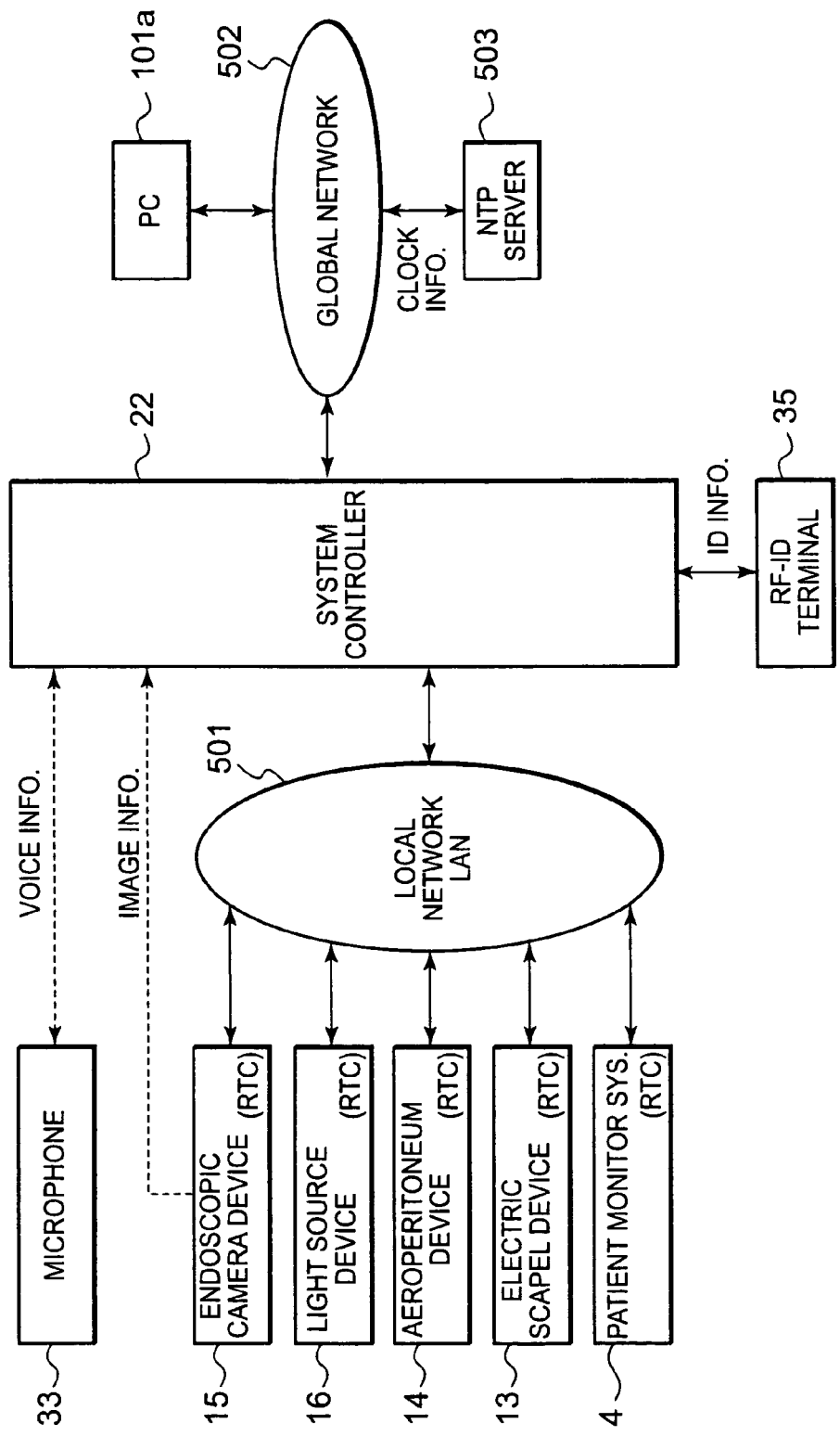
FIG. 13 is a drawing showing a structure of an endoscopic surgical operating system according to a fifth embodiment.
Figure 14:
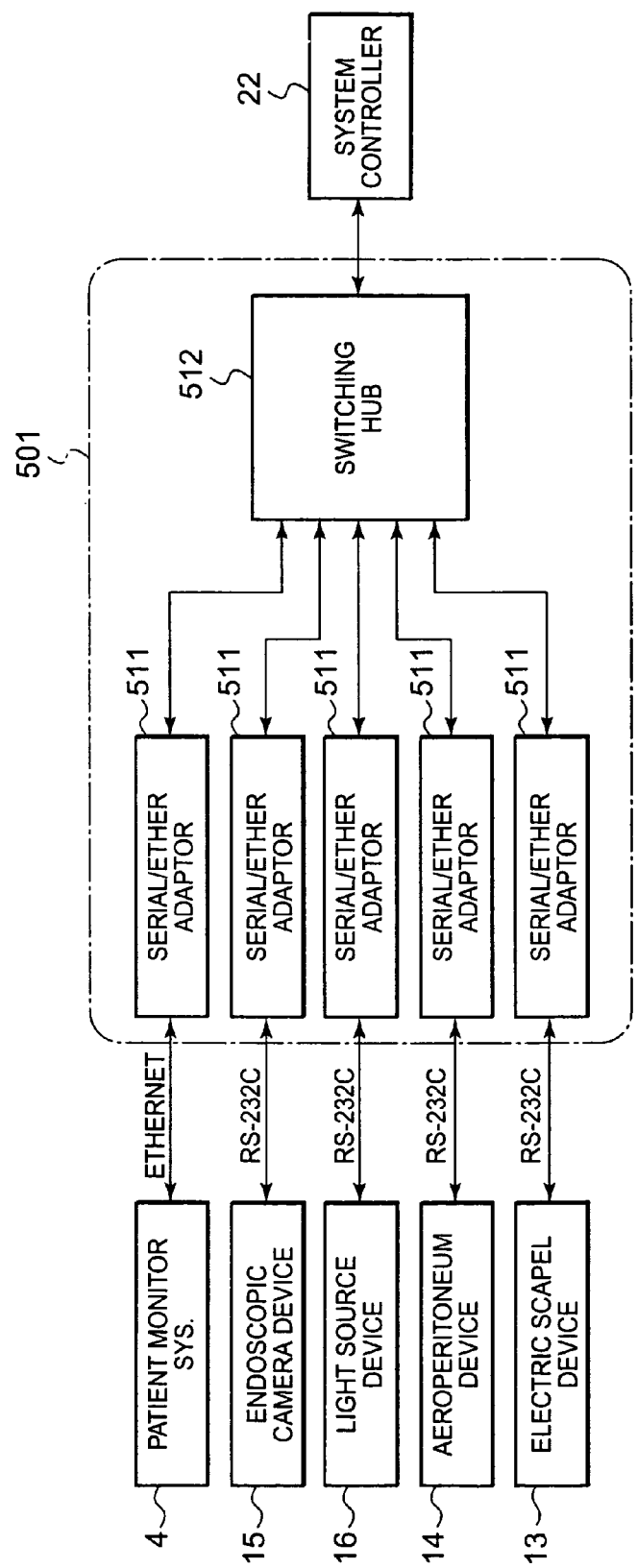
FIG. 14 is a block diagram showing an example of a structure of the local network shown in FIG. 13.

Referring now to FIG. 13 and FIG. 14, the endoscope system according to a fifth embodiment will be described.

FIG. 13 is a drawing showing a structure of the endoscopic surgical operation system, and FIG. 14 is a block diagram showing an example of a structure of a local network in FIG. 13.

The fifth embodiment will be described only where the same differs from the fourth embodiment, and the same structures are represented by the same reference numerals and description will be omitted.

In this embodiment, as shown in FIG. 13, the devices 4, 13-16 which can communicate with the first communication I/F 40 have the RTC, and the system has a local network 501 which is capable of Ethernet® communication as in the fourth embodiment. Then, the system controller 22 obtains the reference clock information from a NTP (Network Time Protocol) server 503 via a global network 502 connected to the PC 101*a*.

The global network 502 is a network having a global address, and obtains an IP address allocated, for example, by a DHCP server.

The structure of implementation of the local network 501 may employ a serial/Ethernet® communication adapter 511 and a switching hub 512 as shown in FIG. 14.

As an implementation of the serial/Ethernet® communication adapter 511, for example, XPort® device from Lantronix Inc. can implement the connecting function to the network economically and in a short time. The XPort® device from Lantronix Inc. is a small package of about 14.5 mm×34 mm×18.25 mm, and all the functions of CPU, memory, and protocol are contained in the RJ45 Ethernet® connector.

At this time, it is necessary to allocate the IP address for the local address to the respective devices in this embodiment. The system controller 22 obtains the data from the respective devices 4, 13-16 via the switching hub 512 based on the IP address.

The PC 101*a* which can be connected to the global network 502 out of the devices which can establish the network connection can adjust the clock information held therein based on the clock information from the NTP server 503.

The system controller 22 can also adjust the clock information held therein based on the clock information from the NTP server 503. Then, the system controller 22 can distribute the clock information to the devices such as the endoscopic camera device 15, the light source device 16, the aeroperitoneum device 14, and the electric scalpel device 13, which can establish local network communication, and these devices can also adjust the clock information held therein.

On the other hand, the system controller 22 can store/reproduce the voice information from the microphone 33 which has no clock information, the image information from the endoscopic camera device 15, and the individual ID information from the RFID terminal 35 added with the clock information at the timing when the information is obtained.

Since the NTP can adjust the clock information regularly at constant cycles, the lag can be prevented from occurring constantly.

It is needless to say that, in the case of the device which cannot establish the network communication with the system controller 22 which has the first communication I/F 40, the system controller 22 can provide the clock information obtained by the NTP to the respective device informations as in the case of the analogue input information such as voice and image, and store and reproduce the same, whereby the same effect as this embodiment is achieved.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope system comprising:
   a plurality of peripheral devices each of which comprises a real time clock and outputs medical information with clock information of the real time clock added;
   a system controller that comprises a reference real time clock and performs communication with the plurality of peripheral devices via a communication interface;
   a storage unit that is provided in the system controller and stores, in at least an initialization, a first time lag as a time lag between the reference clock information of the reference real time clock and the clock information of the real time clock in each of the plurality of peripheral devices;
   a medical information obtaining unit that is provided in the system controller and obtains the medical information outputted from each of the plurality of peripheral devices through the communication interface after the initialization;
   a time lag detecting unit that is provided in the system controller and sequentially detects whether or not a second time lag as a time lag between the clock information added to the medical information obtained by the medical information obtaining unit via the communication interface and the reference clock information of the reference real time clock when the medical information obtaining unit obtains the medical information exceeds the first time lag by a threshold value or more; and
   a control unit that is provided in the system controller and, when the second time lag detected by the time lag detecting unit does not exceed the first time lag by the threshold value or more, adjusts the clock information added to the medical information obtained by the medical information obtaining unit by the clock information of the reference real time clock to be shifted by the first time lag and adjusts obtaining time when the medical information obtaining unit has obtained the medical information to have the time information by the reference clock information which is unified by the reference real time clock, and
   when the second time lag detected by the time lag detecting unit exceeds the first lag time by the threshold value or more, adjusts the clock information added to the medical information obtained by the medical information obtaining unit by the clock information of the reference real time clock to be shifted by the second time lag and adjusts obtaining time when the medical information obtaining unit has obtained the medical information to have the time information by the reference clock information which is unified by the reference real time clock.

2. An endoscope system according to claim 1, wherein the storage unit stores the medical information with the clock information added that is obtained by the medical information obtaining unit from the plurality of peripheral devices so that the clock information is associated with the second time lag information detected by the time lag detecting unit, and
   the endoscope system further comprising a reproducing unit for reproducing medical information of the plurality of peripheral devices stored in the storage unit synchronously based on the unified time information by the reference clock information adjusted by the control unit.

3. An endoscope system according to claim 2, wherein the adjustment of the clock information by the control unit is performed when the medical information including the clock information added by the plurality of peripheral devices is stored in the storage unit of the system controller.

4. An endoscope system according to claim 2, wherein the adjustment of the clock information by the control unit is performed when reproducing the medical information at the reproducing unit.

5. An endoscope system according to claim 2, further comprising
   an image information outputting device that comprises one or more of the plurality of peripheral devices and outputs image information,
   a second storage unit for storing the image information outputted from the image information outputting device, and
   a selecting unit for selecting whether or not the medical information is to be displayed by superimposing on the image information when reproducing the image information by the reproducing unit.

6. An endoscope system according to claim 1, further comprising a transmitting unit for transmitting the medical information and the unified reference clock information corresponding to the medical information which is adjusted by the control unit onto a network as a single unit of data.

7. An endoscope system according to claim 1, wherein the reference clock information of the reference real time clock is adjusted so as to be identical to reference clock information obtained from a server having reference time information.

8. An endoscope system according to claim 1, wherein the storage unit includes a clock information storage area for storing, with respect to all the medical information that the medical information obtaining unit obtains via the communication interfaces, the clock information added to the medical information and information of the second time lag detected by the time lag detecting unit to be associated with each other.

9. An endoscope system according to claim 1,
   wherein each of the plurality of peripheral devices and the system controller are connected to communicate with each other through a communication cable and the communication interface,
   the storage unit stores, in the initialization, a time lag including at least a time lag between the clock information of the reference real time clock and the clock information of the real time clock in each of the plurality of peripheral devices as the first time lag, and
   after the initialization the time lag detecting unit detects the second time lag between the clock information added to the medical information obtained by the medical information obtaining unit via the communication cable and the communication interface and the reference clock when the medical information obtaining unit obtains the medical information.

10. An endoscope system according to claim 1, wherein the control unit forms a clock adjustment unit that adjust, with respect to all the medical information that the medical information obtaining unit obtains after the initialization, the clock information added to the obtained medical information by correction information using the reference clock information.

11. An endoscope system comprising:
one or more first peripheral devices each of which comprises a real time clock and outputs first medical information with clock information of the real time clock added;
one or more second peripheral devices each of which does not have a real time clock and outputs second medical information;
a system controller that comprises a reference real time clock and performs communication with the first peripheral devices and the second peripheral devices via a first communication interlace and a second communication interface, respectively;
a medical information obtaining unit that is provided in the system controller and obtains the medical information outputted from the first and second peripheral devices through the first and second communication interfaces, respectively;
a judging unit that is provided in the system controller and judges whether or not the clock information is added to the first or second medical information obtained by the medical information obtaining unit;
a clock information adding unit that is provided in the system controller and adds reference clock information of the reference real time clock when the medical information obtaining unit obtains the medical information to the second medical information that is obtained by the medical information obtaining unit via the second communication interface and that is judged by the judging unit not to have the clock information added;
a storage unit that is provided in the system controller, stores the second medical information with the reference clock information added and stores, in at least an initialization, a first time lag as a time lag between the reference clock information of the reference real time clock and the clock information of the real time clock in each of the first peripheral devices;
a time lag detecting unit that is provided in the system controller and sequentially detects whether or not a second lag time as a time lag between the clock information added to the first medical information that is obtained by the medical information obtaining unit and the reference clock information of the reference real time clock when the medical information obtaining unit obtains the first medical information exceeds the first lag time stored in the storage unit by a threshold vale or more, with respect to the first medical information that is obtained by the medical information obtaining unit via the first communication interface and that is judged to have the clock information added; and
an adjustment unit that performs adjustment such that, when is it detected by the time lag detecting unit that the second time lag does not exceed the first time lag by the threshold value or more, the clock information added to the first medical information, when the second time lag occurs, is adjusted by the reference clock information of the reference real time clock when the second time lag occurs by an amount equal to an amount of the first time lag, and
when is it detected by the time lag detecting unit that the second time lag exceeds the first time lag by the threshold value or more, the clock information added to the first medical information, when the second time lag occurs, is adjusted by the reference clock information of the reference real time clock when the second time lag occurs.

12. An endoscope system according to claim 11, wherein the storage unit includes a clock information storage area for storing, with respect to all the first medical information which the medical information obtaining unit obtains via the first communication interface, the clock information added to the first medical information and information of the second time lag detected by the time lag detecting unit to be associated with each other.

* * * * *